United States Patent [19]

Uchikawa

[11] Patent Number: 4,666,628
[45] Date of Patent: May 19, 1987

[54] MOISTURE SENSITIVE MATERIAL AND PROCESS FOR ITS PRODUCTION

[75] Inventor: Fusaoki Uchikawa, Itami, Japan

[73] Assignee: Mitsubishi Denki Kabushiki Kaisha, Tokyo, Japan

[21] Appl. No.: 778,225

[22] Filed: Sep. 20, 1985

[30] Foreign Application Priority Data

Dec. 20, 1984 [JP] Japan ............................... 59-268951
Dec. 20, 1984 [JP] Japan ............................... 59-268958

[51] Int. Cl.⁴ ........................................... H01B 1/00
[52] U.S. Cl. ................................ 252/500; 252/506; 252/507; 252/508; 252/511; 252/503; 338/34; 338/35; 43/27 R; 43/29
[58] Field of Search ............... 252/506, 507, 510, 511, 252/518, 519, 520, 503, 508; 338/34, 35; 422/90, 98; 324/71.5; 340/634; 73/27 R, 29; 427/102, 85-87, 38; 419/11, 19, 22, 29, 36, 53-55

[56] References Cited

U.S. PATENT DOCUMENTS

| | | | |
|---|---|---|---|
| 3,864,659 | 2/1975 | Furuuchi et al. | 338/35 |
| 4,157,311 | 6/1979 | Orth | 252/518 |
| 4,378,691 | 4/1983 | Terada et al. | 73/27 R |
| 4,386,336 | 5/1983 | Kinomoto et al. | 338/35 |
| 4,464,647 | 8/1984 | Yokomizo et al. | 252/518 |

Primary Examiner—Josephine L. Barr
Attorney, Agent, or Firm—Oblon, Fisher, Spivak, McClelland & Maier

[57] ABSTRACT

A moisture sensitive material comprising a fired product consisting essentially of at least one member selected from the group consisting of a metal oxide and graphite, and a polymerized organo-silicon compound, and at least one member selected from the group consisting of alkali metal ions and halogen ions, doped on the fired product.

4 Claims, 5 Drawing Figures

MOISTURE SENSITIVE MATERIAL AND PROCESS FOR ITS PRODUCTION

The present invention relates to a moisture sensitive material and a process for its production. More particularly, the present invention relates to a moisture sensitive material for a moisture sensor which detects a relative humidity of an atmosphere by utilizing a change in the electrical resistance of the material and a process for its production.

Recently, metal oxide ceramics which are stable both physically and chemically against an atmosphere and which have high strength have been most commonly employed as moisture sensitive materials having the above-mentioned function.

In the moisture sensitive mechanism of a moisture sensitive material made of such a conventional ceramic, a phenomenon is utilized in which the concentration of hydrogen ions ($H^+$) generated by dissociation of water vapor at the surface of the porous ceramic varies depending on the relative humidity of the surrounding, whereby the electrical resistance of the moisture sensitive section varies.

As shown in the following publication, when the relative humidity is low, the $H^+$ ions conduct on hydroxyl groups formed on the surface of the material by hopping, when the relative humidity is high, hydrated $H^+$ ions conduct through a water film in the same way as in an aqueous solution. (J. H. Anderson and G. A. Parks; J. Phys. Chem., Vol. 72 published in 1968, page 3662)

A moisture sensitive material made of the above-mentioned conventional ceramic utilizes the electrical conduction by $H^+$ to detect moisture.

In order to obtain adequate sensitivity, the electrical resistance of the moisture sensitive material had a lower limit (about 500 K$\Omega$ when the relative humidity is 50%, about 20 K$\Omega$ when the relative humidity is 90%). When a moisture sensor made of the above-mentioned ceramic was employed for automatic moisture control for an air conditioner, the electrical resistance was too high from the viewpoints of the driving and adaptability in the detector circuit, and it was difficult to obtain a sensor having good adaptability.

In most conventional ceramic moisture sensitive materials which utilize an electrical conduction by $H^+$, it is unavoidable that the electrical resistance of the sensor changes substantially as time passes, because OH groups tend to be chemically stably adsorbed on the surface as the adsorption and desorption of water (moisture) is repeated when the material is used or left in air.

Therefore, it is necessary to have the changed resistance characteristics recovered to the initial characteristics, by providing a heater around the moisture sensitive material, at a covering, in a substrate or at electrodes, to electrically heat the material at a temperature of from 500° to 600° C., as shown in Japanese Unexamined Utility Model Publication Nos. 161248/1980 and 161249/1980, Japanese Unexamined Patent Publication Nos. 61788/1977, 70895/1979, 101399/1979, 87941/1980, 2542/1981, 109044/1981 and 160649/1981.

The present invention has been made to solve such a problem, and it is an object of the present invention to obtain a moisture sensitive material with its moisture sensitive characteristics stabilized for a long period of time without requiring a heating equipment (heater) for the prevention of deterioration with time.

Namely, it is an object of the present invention to obtain a moisture sensitive material having a low electrical resistance and being highly suitable for an electric circuit.

It is a further object of the present invention to provide a process for producing a moisture sensitive material having good water-proof properties with its resistance highly stable without substantial deterioration with time.

The present invention provides a moisture sensitive material comprising a fired product consisting essentially of at least one member selected from the group consisting of a metal oxide and graphite, and a polymerized organo-silicon compound, and at least one member selected from the group consisting of alkali metal ions and halogen ions, doped on the fired product.

The present invention also provides a process for producing a moisture sensitive material, which comprises a step of mixing at least one member selected from the group consisting of a metal oxide and graphite, and polymerized organo-silicon compound, a step of firing the mixture to obtain a fired product, a step of applying at least one member selected from the group consisting of alkali metal ions and halogen ions to the fired product, and a step of firing the ion-doped product thereby obtained.

As the polymerized organo-silicon compound of the present invention, there may be employed a substance which becomes porous by firing such as methyl silicone, methylphenyl silicone and ethyl silicate. The substance acts as a binding agent for the metal oxide and/or graphite.

Because of the porous structure, the effects of the metal oxide and/or the graphite in the moisture sensitive material of the present invention clearly appear, and water is adsorbed in a large quantity, whereby it is possible to obtain a moisture sensitive material having a low electrical resistance.

As the metal oxide of the present invention, there may be employed, e.g. at least one member selected from the group consisting of oxides of Al, Cu, Ni, Cr and Ti.

As the alkali metal ions of the present invention, there may be employed, e.g. at least one type of ions selected from the group consisting of potassium ions, sodium ions and lithium ions in the form of one of compounds such as nitrates, sulfates, carbonates and halides of the respective alkali metals.

As the halogen ions of the present invention, there may be employed, e.g. at least one type of ions selected from the group consisting of chlorine ions and fluorine ions.

In the moisture sensitive material of the present invention, the preferred amount of the doped ions is from 0.05 to 0.5 parts by weight relative to the fired product.

In the process for producing a moisture sensitive material of the present invention, the ion doping step is preferably conducted by dipping the fired product into a solution containing from 0.02 to 0.1 mols/liter of alkali metal or halogen ions.

In the moisture sensitive material of the present invention, the fired product preferably contains from 250 to 350 parts by weight of at least one member selected from the group consisting of a metal oxide and graphite, and 100 parts by weight of a polymerized organo-silicon compound.

In the process for producing the moisture sensitive material of the present invention, from 50 to 100 parts by weight of at least one member selected from the group consisting of a metal oxide and graphite is preferably mixed with 100 parts by weight of the polymerized organo-silicon compound.

In the process of the present invention, the mixture is preferably fired at a temperature of from 450° to 600° C. for from 1 to 2 hours and the ion-doped product is preferably fired at a temperature of from 400° to 550° C. for from 0.5 to 1 hours.

The moisture sensitive material of the present invention may contain a powder of inorganic material such as a metal oxide e.g. $Al_2O_3$ and mica, talc and $SiO_2$ as an additive to improve the coat-forming effect, the acceleration of drying and curing, the prevention of cracking and to improve the bonding performance to the substrate.

Figure 1:
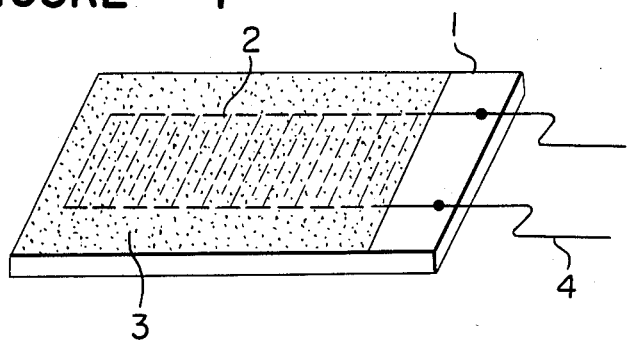
FIG. 1 is a perspective view of a moisture sensor employing the moisture sensitive material of the present invention.

Now, the present invention will be described in detail with reference to Examples. However, it should be understood that the present invention is by no means restricted by these specific Examples.

EXAMPLE 1

A Pt-Pd alloy paste was printed on an alumina insulating substrate by screen printing to form comb-shaped electrodes with ten teeth at intervals of 0.2 mm, and after a Pt lead was bonded to each electrode, the substrate was baked.

A thinner was added to Composition 1 indicated below, and the mixture was stirred with a stirrer, and the substrate was dipped in the mixture to form a coat having a thickness of about 50 μm.

After being fired at 480° C. for two hours, the above-mentioned substrate was dipped into a 5% $Na_2CO_3$ solution in a solvent mixture of water-alcohol, at 25° C. for one minute, and then it was fired again at 450° C. for an hour to obtain a moisture sensitive coat. Thus, a moisture sensor shown in FIG. 1 was prepared.

In the Figure, reference numeral 1 indicates an insulating substrate, numeral 2 is an electrode, numeral 3 is a moisture sensitive coat, and numeral 4 is a lead wire.

Composition 1

Polymerized organo-silicon compound:

| Methyl silicone | 61.4% by weight |
| Graphite | 27.6% by weight |
| Additive: $SiO_2$ | 11% by weight |

Two samples, i.e. a moisture sensor employing a moisture sensitive material of Example 1 of the present invention thus obtained, and a conventional type of a ceramic moisture sensor prepared in the same manner as in FIG. 1 except that a moisture sensitive coat was made of $Al_2O_3$-MgO-ZnO type ceramic sintered at 1250° C. for four hours, were subjected to comparative measurement of their moisture sensitive characteristics (relative humidity (%)−eletrical resistance (Ω)) and changes with time thereof.

Figure 2:
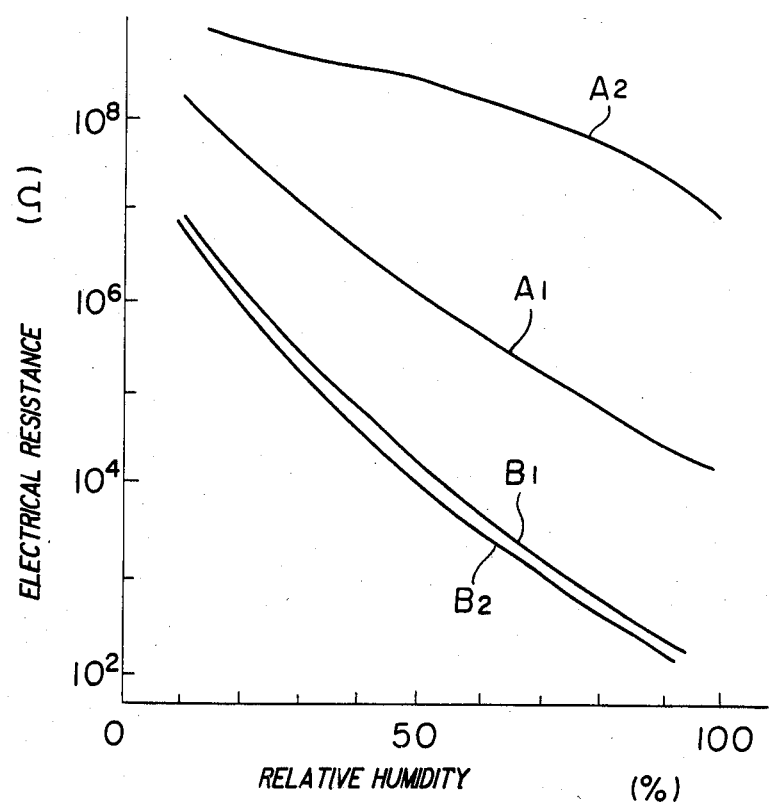
FIGS. 2 to 5 are graphs showing comparisons between moisture sensitive characteristics of sensors of the present invention and those of conventional moisture sensors.

Thus, the results shown in FIG. 2 were obtained. The impressed voltage was IV and 50 Hz.

In FIG. 2, curve $A_1$ shows initial moisture sensitive characteristics of the conventional type moisture sensor and curve $A_2$ shows the same characteristics after storage at room temperature for six months.

Curve $B_1$ shows initial moisture sensitive characteristics of the moisture sensor employing the moisture sensitive material of Example 1 of the present invention and curve $B_2$ shows the same characteristics after storage at room temperature for six months.

It is evident from the Figure that after the storage for six months, the resistance of the moisture sensor employing a conventional $H^+$ conduction type ceramic as a moisture sensitive material, was some hundreds times as large as the initial value, and the moisture sensitive function became extremely poor. Whereas, the resistance of the moisture sensor employing the moisture sensitive material of Example 1 of the present invention became only slightly lower and no reduction of the moisture sensitive function was observed after the storage for six months.

As is evident from the comparison between the initial moisture sensitive characteristics curves $A_1$ and $B_1$, the moisture sensor employing the moisture sensitive material of Example 1 of the present invention has at most one tenth of the resistance value of the conventional moisture sensor and higher adaptability in a circuit and better moisture sensitivity.

It is believed that the moisture sensor employing the moisture sensitive material of Example 1 of the present invention shows the low resistance and the good sensitivity, because alkali metal ions ($Na^+$ in this case) existing in the interlayer structure of graphite are fetched through the adsorbed water on the surface of the moisture sensitive section to participate in the surface electrical conduction and the moisture sensitive material becomes more porous by the second firing.

EXAMPLE 2

Toluene was added to Composition 2 indicated below, and the mixture was stirred with a stirrer. The mixture was applied to a substrate similar to the one employed in Example 1, on which Pt-Pd type electrodes were formed and baked, by dipping treatment to form a coat having a thickness of 20 μm.

The substrate was dried at a temperature of 80° C. for thirty minutes, and then it was fired at 580° C. for two hours, followed by dipping it into a 3% aqueous solution of $FeCl_2$ at 25° C. for thirty seconds.

After the dipping, it was fired at 500° C. for an hour to produce a moisture sensor with a moisture sensitive material of the present invention.

Composition 2

Polymerized organo-silicon compound:

| Methylphenyl silicone | 67.4% by weight |
| Graphite | 13.6% by weight |
| Additives: $Al_2O_3$ | 10.3% by weight |
| Mica | 8.7% by weight |

Two samples, i.e. the sensor thus obtained and a conventional ceramic moisture sensor prepared in the same manner as in FIG. 1 except that the moisture sensitive coat was made of $SiO_2$-MgO-$TiO_2$ type ceramic sintered by heat treatment at 1150° C. for five hours, were subjected to measurement of their moisture sensitive characteristics and changes with time thereof.

Figure 3:
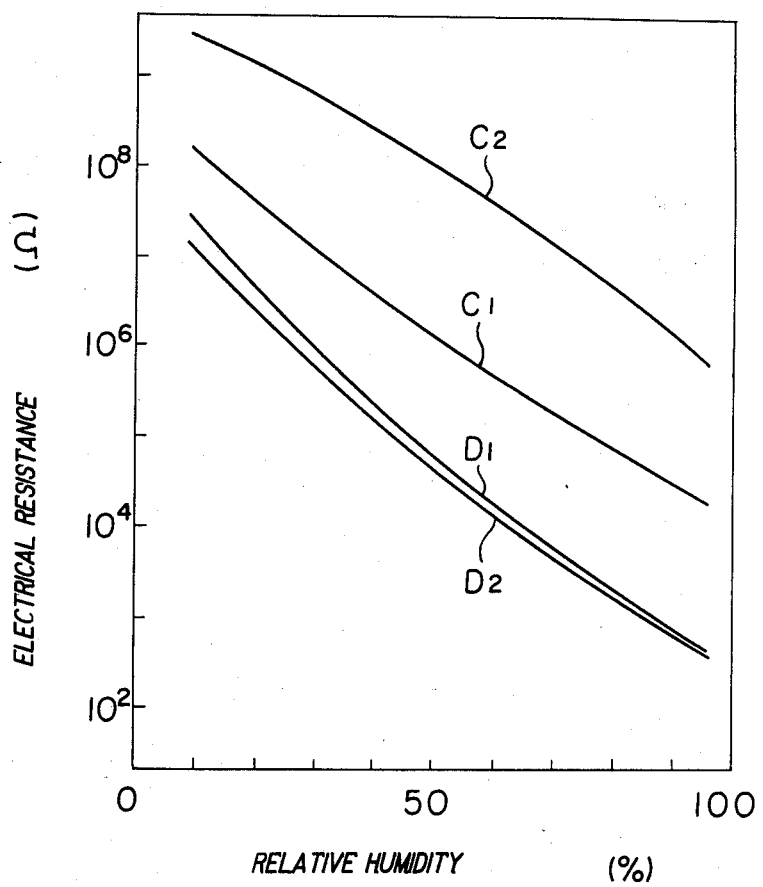

Thus, the results shown in FIG. 3 were obtained. In FIG. 3, curve $C_1$ shows initial moisture sensitive characteristics of the conventional type moisture sensor and curve $C_2$ shows the same characteristics after storage at room temperature for six months.

Curve $D_1$ shows initial moisture sensitive characteristics of the moisture sensor employing the moisture sensitive material of the present invention and curve $D_2$ shows the same characteristics after storage at room temperature for six months.

EXAMPLE 3

Xylene was added to Composition 3 indicated below, and the mixture was stirred with a stirrer. The mixture was applied to a substrate similar to the one employed in Example 1, on which Pt-Pd type electrodes were formed and baked, by dipping treatment to form a coat having a thickness of 30 μm.

The substrate was dried at 120° C. for thirty minutes, and then it was fired at 520° C. for two hours, followed by dipping it into a 2% aqueous solution of LiCl at 25° C. for twenty seconds.

After the dipping, it was fired at 480° C. for an hour to produce a moisture sensor with a moisture sensitive material of the present invention.

Composition 3

Polymerized organo-silicon compound:

| Methylphenyl silicone | 52.3% by weight |
| Graphite | 24.8% by weight |
| Additives: Talc | 12.9% by weight |
| $SiO_2$ | 10.0% by weight |

Two samples, i.e. the sensor thus obtained and a conventional ceramic moisture sensor prepared in the same manner as in FIG. 1 except that the moisture sensitive coat was made of $Cr_2O_3$-CaO type ceramic sintered by heat treatment at 1450° C. for four hours, were subjected to measurement of their moisture sensitive characteristics and changes with time thereof.

Figure 4:
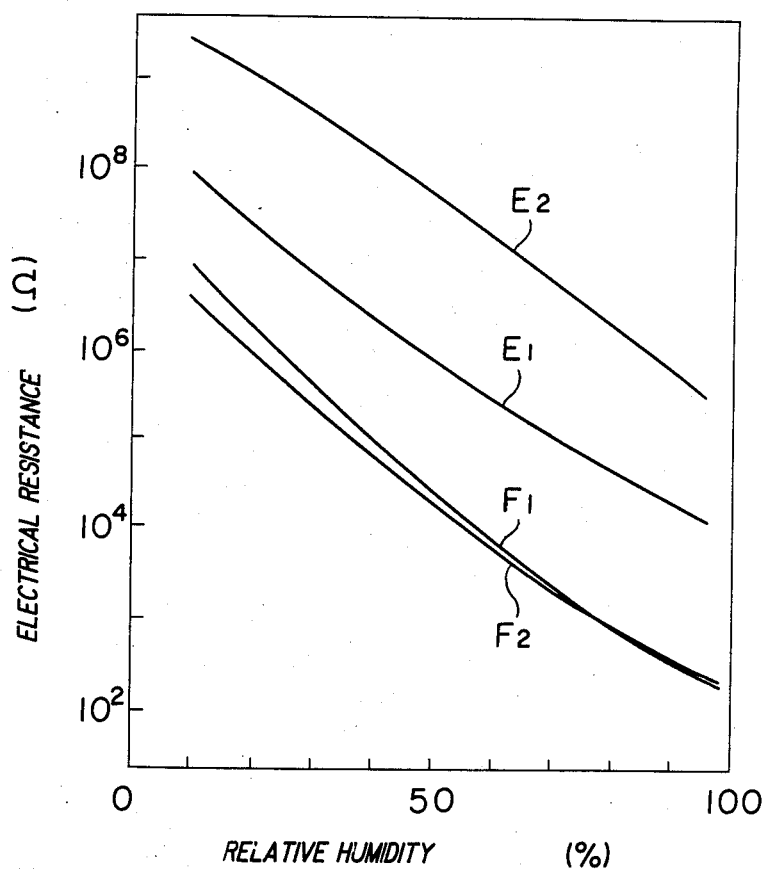

Thus, the results shown in FIG. 4 were obtained. In FIG. 4, curve $E_1$ shows initial moisture sensitive characteristics of the conventional type moisture sensor and curve $E_2$ shows the same characteristics after storage at room temperature for six months.

Curve $F_1$ shows initial moisture sensitive characteristics of the moisture sensor employing the moisture sensitive material of the present invention and curve $F_2$ shows the same characteristics after storage at room temperature for six months.

It is evident from each of FIGS. 3 and 4 that after the storage for six months, the resistance of the moisture sensor employing the conventional $H^+$ type ceramic as the moisture sensitive material, was at least ten times as large as the initial value, and the moisture sensitive function became extremely poor. Whereas, the resistance of the moisture sensors employing the moisture sensitive materials of Examples 2 and 3 of the present invention became only slightly lower and no reduction of the moisture sensitive function was observed even after the storage for six months.

Like Example 1, the sensors employing moisture sensitive materials of the present invention have about one tenth of the resistance value of the conventional moisture sensors.

It is believed that as halogen ions (in Example 2: $Cl^-$) were doped by dipping the substrate into the aqueous solution of $FeCl_2$ so that they take part in the electrical conduction, good results mentioned above can be obtained.

Similarly, in Example 3, it is believed that as alkali ions ($Li^+$) and halogen ions participate in the electrical conduction, good results mentioned above can be obtained.

EXAMPLE 4

A thinner was added to Composition 4 indicated below, and the mixture was stirred with a stirrer. The mixture was applied to the substrate similar to the one employed in Example 1, on which Pt-Pd type electrodes were formed and baked, by dipping treatment to form a coat having a thickness of about 50 μm.

After being fired at 530° C. for one and a half hours, the above-mentioned substrate was dipped into a 5% aqueous solution of $K_2SO_4$ for thirty seconds to obtain a moisture sensitive coat 3, thus a moisture sensor shown in FIG. 1 was obtained.

Composition 4

Polymerized organo-silicon compound:

| Methylphenyl silicone | 55.6% by weight |
| Metal oxides: $TiO_2$ | 20.3% by weight |
| $Cr_2O_3$ | 18.4% by weight |
| Additive: $SiO_2$ | 5.7% by weight |

EXAMPLE 5

The same composition as employed in Example 4 was applied to a substrate, and the substrate was fired and dipped into a $K_2SO_4$ aqueous solution in the same manner as in Example 4.

Further, the substrate was fired at 400° C. for thirty minutes to produce a moisture sensor employing a moisture sensitive material of the present invention.

Three samples, i.e. moisture sensors employing moisture sensitive materials of Examples 4 and 5 of the present invention produced in the above-mentioned process, and a conventional type ceramic moisture sensor prepared in the same manner as in FIG. 1 except that a moisture sensitive coat was made of $Al_2O_3$-MgO-ZnO type ceramic sintered at 1250° C. for four hours, were subjected to comparative measurement of their moisture sensitive characteristics (relative humidity (%) — electrical resistance (Ω)) and changes with time thereof.

Figure 5:
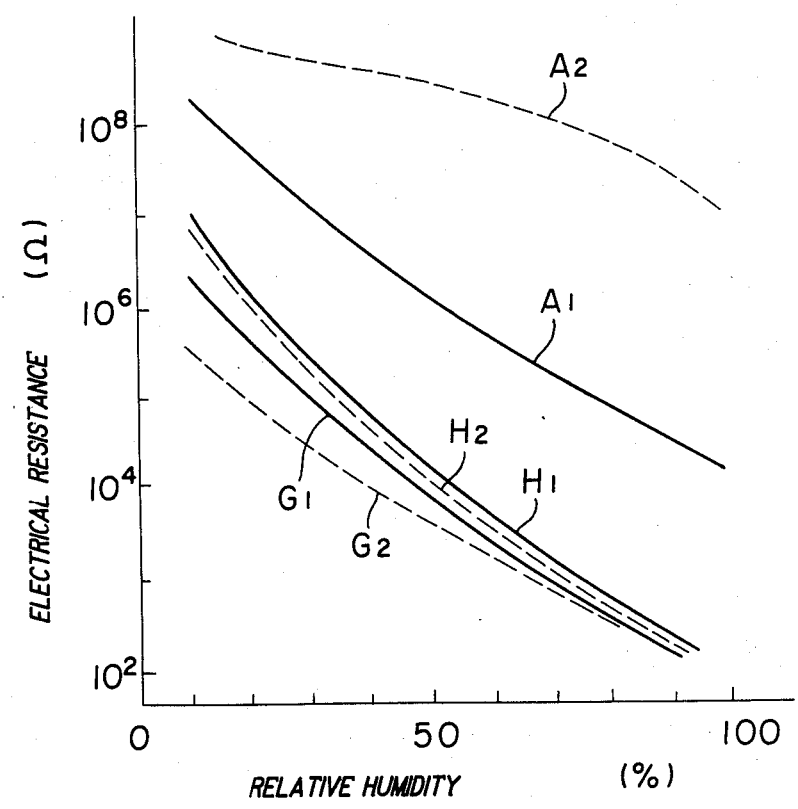

Thus, results shown in FIG. 5 were obtained. The impressed voltage was 1 V and 50 Hz.

In FIG. 5, curve $A_1$ shows initial moisture sensitive characteristics of the conventional type moisture sensor and curve $A_2$ shows the same characteristics after storage at room temperature for a year.

Curve $G_1$ shows initial moisture sensitive characteristics of the moisture sensor employing the moisture sensitive material of Example 4 of the present invention and curve $G_2$ shows the same characteristics after storage at room temperature for a year.

Curve $H_1$ shows initial moisture sensitive characteristics of the moisture sensor employing the moisture sensitive material of Example 5 of the present invention and curve $H_2$ shows the same characteristics after storage at room temperature for a year.

It is evident from FIG. 5 that after the storage for one year, the resistance of the moisture sensor employing a conventional $H^+$ conduction type ceramic as a moisture sensitive material, was some hundreds times as large as the initial value, and the moisture sensitive function became extremely poor. Whereas, in the moisture sensors employing the moisture sensitive materials of Examples 4 and 5 of the present invention, the reduction in the electrical resistance was minimum even after the storage for one year.

As is evident from the comparison between the initial moisture sensitive characteristics curves $A_1$ and $G_1$, or $A_1$ and $H_1$, the moisture sensor employing the moisture sensitive material of Example 4 or 5 of the present invention has at most one tenth of the resistance value of the conventional moisture sensor and higher adaptability in a circuit and better moisture sensitivity, particularly in the case of $H_1$.

It is believed that the moisture sensor employing the moisture sensitive material of the present invention has the low resistance because the alkali metal ions ($K^+$ in this case) are fetched through the adsorbed water on the surface of the moisture sensitive section to participate in the electrical conduction at the surface. Particularly, in the case of Example 5, the moisture sensitive material becomes more porous by the second firing, and the water adsorptivity increases, whereby the sensitivity is improved and the resistance hardly lowers with time.

Alkali metal ions or halogen ions may be doped also by ion plantation, vacuum evaporation, etc. to obtain substantially the same effect as obtainable by the above mentioned dipping method.

According to the present invention, it is possible to obtain a moisture sensitive material with its moisture sensitive characteristics being stable for a long period of time without requiring a heating equipment (heater) for the prevention of deterioration with time, and the moisture sensitive material is useful for e.g. a moisture sensor.

The strength of the coat of the moisture sensitive material increases because of the presence of the metal oxide, whereby the quantity of water adsorbable in the moisture sensitive material becomes greater and the resistance of the material becomes lower.

The alkali metal ions and halogen ions are fetched through the adsorbed water on the surface of the moisture sensitive section to participate in the electrical conduction at the surface, whereby the resistance of the moisture sensitive material becomes lower.

The graphite in the present invention serves to stabilize the alkali metal ions and halogen ions, and to facilitate the adsorption and desorption of water.

I claim:

1. A moisture sensitive material comprising a fired product consisting essentially of 250 to 350 parts by weight of at least one member selected from the group consisting of a metal oxide of Al, Cu, Ni, Cr and Ti and graphite, and 100 parts by weight of a polymerized organo-silicon compound, and at least one member selected from the group consisting of potassium, sodium and lithium ions and chlorine and fluorine ions, doped on the fired product in an amount of 0.05 to 0.5 parts by weight.

2. The moisture sensitive material according to claim 1, wherein the polymerized organo-silicon compound is methyl silicone, methylphenyl silicone or ethyl silicate.

3. A process for producing a moisture sensitive material, which comprises a step of mixing 50 to 100 parts by weight of at least one member selected from the group consisting of metal oxide of Al, Cu, Ni, Cr and Ti and graphite, and 100 parts of a polymerized organo-silicon compound, a step of firing the mixture at a temperature of 450°–600° C. to obtain a fired product, a step of doping at least one member selected from the group consisting of potassium, sodium and lithium ions and chlorine and fluorine ions to the fired product, and a step of firing the ion-doped product thereby obtained at a temperature of from 400° to 550° C.

4. The process for producing a moisture sensitive material according to claim 3, wherein the ion doping step is conducted by dipping the fired product into a solution cotaining from 0.2 to 0.1 ml/liter of the ions.

* * * * *